(12) United States Patent
Niederberger et al.

(10) Patent No.: US 9,696,214 B2
(45) Date of Patent: Jul. 4, 2017

(54) PORTABLE ELECTRONIC DEVICE WITH INSIDE TEMPERATURE CALIBATION

(71) Applicant: Sensirion AG, Stafa (CH)

(72) Inventors: Dominik Niederberger, Zurich (CH); Andrea Sacchetti, Zurich (CH); Dominic Boni, Dielsdorf (CH)

(73) Assignee: Sensirion AG, Stafa (CH)

( * ) Notice: Subject to any disclaimer, the term of this patent is extended or adjusted under 35 U.S.C. 154(b) by 210 days.

(21) Appl. No.: 14/264,581

(22) Filed: Apr. 29, 2014

(65) Prior Publication Data

US 2014/0328367 A1 Nov. 6, 2014

(30) Foreign Application Priority Data

May 6, 2013 (EP) .................................... 13002392

(51) Int. Cl.
*G01K 1/20* (2006.01)
*G01K 7/42* (2006.01)
(Continued)

(52) U.S. Cl.
CPC ............... *G01K 1/20* (2013.01); *G01K 7/42* (2013.01); *G01K 15/005* (2013.01); *H04M 1/21* (2013.01); *H04M 2250/12* (2013.01)

(58) Field of Classification Search
USPC .......................................................... 374/1
See application file for complete search history.

(56) References Cited

U.S. PATENT DOCUMENTS 3,817,453 A 6/1974 Pinckaers
4,096,575 A 6/1978 Itoh
(Continued)

FOREIGN PATENT DOCUMENTS

DE 102011101355 11/2012
EP 0387025 9/1990
(Continued)

OTHER PUBLICATIONS

European Search Report No. in Application No. 13002392.2 dated Oct. 29, 2013.

*Primary Examiner* — Minh Phan
*Assistant Examiner* — Leon W Rhodes, Jr.
(74) *Attorney, Agent, or Firm* — Cooper & Dunham

(57) ABSTRACT

In a portable electronic device, a temperature sensor (1) is provided for sensing an ambient temperature ($T_R$) of the portable electronic device. At least one other temperature sensor (3) is provided for sensing a temperature ($T_I$) inside the portable electronic device. The portable electronic device further comprises a set of components (2) radiating heat in an active state in response to the consumption of electrical energy. A calibration module (5) is adapted to conduct a calibration measurement during or in response to an active state of at least a first component out of the set, and is adapted to determine a set of calibration parameters (c1) in response to the calibration measurement for adjusting the at least one sensed inside temperature ($T_1$). A compensator (4) is provided for determining a compensated ambient temperature ($T_A$) dependent on at least the sensed ambient temperature ($T_S$) and the at least one adjusted sensed inside temperature (c1, $T_1$).

15 Claims, 2 Drawing Sheets

(51) Int. Cl.
  *G01K 15/00* (2006.01)
  *H04M 1/21* (2006.01)

(56) References Cited

U.S. PATENT DOCUMENTS

| | | | |
|---|---|---|---|
| 5,199,637 A | 4/1993 | Adams | |
| 5,502,838 A | 3/1996 | Kikinis | |
| 5,603,101 A | 2/1997 | Choi | |
| 5,721,837 A | 2/1998 | Kikinis et al. | |
| 5,926,778 A * | 7/1999 | Poppel | G01L 19/04 702/130 |
| 6,697,645 B1 | 2/2004 | MacFarlane | |
| 6,912,386 B1 | 6/2005 | Himberg et al. | |
| 7,027,834 B2 | 4/2006 | Soini et al. | |
| 7,181,357 B1 * | 2/2007 | Rotem | G01K 15/00 374/110 |
| 7,280,301 B1 | 10/2007 | Jackson et al. | |
| 7,364,353 B2 | 4/2008 | Kolk | |
| 8,237,515 B2 * | 8/2012 | Keating | H03B 5/04 331/158 |
| 2008/0143522 A1 | 6/2008 | Sung | |
| 2008/0317086 A1 * | 12/2008 | Santos | G01K 7/00 374/1 |
| 2009/0144014 A1 | 6/2009 | Aljabari | |
| 2010/0268475 A1 * | 10/2010 | Kusumoto | G01N 27/3274 702/19 |
| 2010/0307916 A1 | 12/2010 | Ramey et al. | |
| 2011/0119018 A1 | 5/2011 | Skarp | |
| 2011/0307208 A1 | 12/2011 | Graf et al. | |
| 2012/0224602 A1 | 9/2012 | Crafts et al. | |
| 2013/0121367 A1 * | 5/2013 | Ahuja | G01C 25/00 374/1 |
| 2014/0328368 A1 | 11/2014 | Niederberger et al. | |

FOREIGN PATENT DOCUMENTS

| | | |
|---|---|---|
| EP | 1301014 | 4/2003 |
| JP | 2010101741 | 5/2010 |
| WO | 0169341 | 9/2001 |
| WO | 2013045897 | 4/2013 |
| WO | 2014005235 | 1/2014 |

* cited by examiner

PORTABLE ELECTRONIC DEVICE WITH INSIDE TEMPERATURE CALIBATION

CROSS REFERENCES TO RELATED APPLICATIONS

This application claims the priority of European patent application 13002392.2, filed May 6, 2013, the disclosure of which is incorporated herein by reference in its entirety.

TECHNICAL FIELD

The present invention relates to a portable electronic device, to a method for operating a portable electronic device, and to a computer program element for operating a portable electronic device.

BACKGROUND ART

It is desired to conduct a precise measurement of the ambient temperature with a portable electronic device such as a mobile phone or a portable computing device such as a tablet computer, which portable electronic device typically comprises a processor and/or a display generating heat during operation.

DISCLOSURE OF THE INVENTION

According to a first aspect of the present invention, a portable electronic device is provided.

The portable electronic device comprises a temperature sensor for sensing a temperature ambient the portable electronic device which temperature sensor typically provides a sufficient coupling to the environment of the portable electronic device, e.g. by being exposed to the ambient through openings in a housing of the device or other means. However, given that the portable electronic device, which may be a mobile phone or a portable electronic computing device in one embodiment, typically comprises components that in an active state consume electrical power and thereby release heat, such as a central processing unit and/or a display, the ambient temperature sensed by the temperature sensor may be impacted in view of heat migrating from such components to the temperature sensor. This may result in that the temperature sensed by the temperature sensor no longer reflects the real ambient temperature but reflects the real ambient temperature perturbed by the self-heating of the device.

Hence, the present portable electronic device comprises at least one other temperature sensor for sensing a temperature inside the portable electronic device. Such other temperature sensor/s may be arranged inside a casing of the portable electronic device, and for example, may provide a good thermal coupling to an assigned component in case a temperature of this component shall be sensed. For example, in case the temperature of a central processing unit of the device shall be sensed by such other temperature sensor, it may be preferred that this other temperature sensor is arranged close to the central processing unit, and possibly may be integrated as a resistive temperature sensor into a chip containing the central processing unit. For example, in case the temperature of a rechargeable battery of the device shall be sensed by another temperature sensor, it may be preferred that this other temperature sensor is arranged close to the battery including a sufficient thermal coupling to the battery. However, in other embodiments, one or more other temperature sensors may be arranged in the casing of the portable electronic device without being specifically assigned to a heat radiating component but may be arranged at a location on the circuit board. Hence, the one or more other temperature sensors may sense temperatures at different locations within the device.

In addition, the present portable electronic device comprises a compensator for determining a compensated ambient temperature which preferably better reflects the real ambient temperature. This compensated ambient temperature represents an estimate of the real ambient temperature based on the sensed ambient temperature as supplied by the temperature sensor and by taking into account the heat generated by at least one heat releasing electronic component of the device sensed by at least one other temperature sensor. As a result, the sensed ambient temperature preferably may be corrected by a temperature value owed to the heat generated from the subject component and transferred therefrom to the temperature sensor. As a result, the compensated ambient temperature may be determined dependent on the sensed ambient temperature and the one or more sensed inside temperatures. In a preferred embodiment, the compensator comprises a compensation model for modelling an impact of the heat on the sensed inside temperature/s and propagated via one or more heat paths to the temperature sensor for sensing the ambient temperature.

However, the one or more other temperature sensors used in such portable electronic device may not necessarily provide the correct inside temperature but may suffer from an offset or other manufacturing, circuit related or aging effects. Hence, it is preferred to calibrate these one or more other temperature sensors. This may be achieved by a calibration module which preferably is embodied as software to be executed on the central processing unit of the portable electronic device. The calibration module is adapted to conduct a calibration measurement during or in response to an active state of at least a first component of the set. Hence, it is envisaged to conduct a temperature measurement while at least the first component is active, i.e. consumes electrical power and radiates heat. The heat or a portion thereof then is measured by the one or more of the other temperature sensors. It may be preferred that a measurement of the inside temperature/s for calibration purposes is not taken immediately after activating at least the first component, but little after such that it can be assumed that the heat radiated from at least the first component has reached a more or less constant level and has reached to the location/s of the other temperature sensor/s. Such state is also denoted as steady state. In a first embodiment, the temperature measurements may be taken after at least a time x, such as two seconds, has passed since starting applying the load, within which time x it assumed to have reached a steady state in heat generation and distribution. In another embodiment, the trigger for taking the temperature measurements may be subject to a sensed inside temperature. For example, the first component is the central processing unit, a temperature sensed inside close to the central processing unit may require to reach a defined level for taking the temperature measurements assuming that when this threshold temperature is reached, the steady state is reached. In another embodiment, in addition or alternatively to triggering the measurement subject to the sensed inside temperature at at least one location, the measurement is triggered subject to a history of the the/a sensed inside temperature, which may include evaluating the dynamics of the sensed inside temperature starting with applying the load to the first component including its slope. The slope may be used as an indicator if the heat generation and distribution already is in or is close to a steady state. In a steady state, it can be assumed that a rise of the sensed inside temperature will only be small over time. If, however, the rise of the sensed inside temperature exceeds a threshold indicating at least a medium rise, it may safely be assumed that the steady state is not reached yet given that the heat still builds up at the measurement location. Hence, these embodiments refer to the desire to accept sensed temperature values for the calibration purposes only at a time at which it can be assumed that the heat generated by at least the first component has ramped up to its desired value, remains stable there and is sufficiently distributed such that a state close to a thermal steady state is reached. In an alternative, the measurement of the inside temperature/s for calibration purposes may yet be taken after at least the first component has been deactivated again given that the radiated heat may not immediately drop. Hence, it is preferred to conduct the calibration measurement during the active state of the at least first component or in response to the active state.

It is preferred that the active state not only radiates any amount of heat but a defined heat. The defined heat manifests in predictable inside temperatures at the location/s of the other temperature sensor/s.

One or more components of the set may be active during a calibration measurement subject to the calibration strategy. Preferably, the set of components comprises the components of the device that have a significant impact on the sensed ambient temperature when being active and radiating heat, and that on the other hand are required to take a defined state during the calibration measurement in view of their significant impact. For example, a sample set for a mobile phone or a tablet computer may include a central processing unit, an energy storage, a display, and a radio frequency transmission unit. It is preferred that the components of this set each are in a defined state during the calibration measurement. A state may at minimum be one of an active state or an inactive state where it is assumed that in the active state heat is radiated by this component while in the inactive state no (major) amount of heat is radiated. However, it is not required that the subject component is not consuming any electrical energy in the inactive state. Components may be in the inactive sleep mode, for example, but not be completely switched off. However, in the sleep mode, energy consumed is negligible and the resulting heat at least has no impact on the ambient temperature sensing.

Note that for the calibration measurement, once the set of components is properly selected, it is preferred that all components of the set are in a predefined state. At least one component of the set, denoted as first component is in an active state during the calibration measurement. In case the set includes only one component, such as the central processing unit, or alternatively the energy storage, this component at the same time constitutes the first component that is active during the calibration measurement. However, in case there are several components in the set it still may be only a first component out of the set being active during the calibration measurement while the rest of the components of the set is inactive. In this embodiment, it may only be the component switched active during the calibration measurement that radiates most heat in the set. However, there are other embodiments in which several calibration measurements are conducted sequentially in order to determine the set of calibration parameters. In a first round it may be the central processing unit being active and the other components being inactive, while in a second round the display is active and the other components are inactive, and so forth.

In another embodiment, there are more than one component of the set simultaneously active during a calibration measurement such as two or even all components of the set. In all these embodiments, it is desired to determine upfront expected inside temperature/s or an expected compensated ambient temperature in response to the active state/s.

In one embodiment, the defined states of the components or at least of a subset of components are actively effected by the calibration module. Hence, the calibration module may actively control the at least first component in an active state, and may deactivate the other components of the set, for example. In another variant, however, the calibration module may during a regular operation of the device at some point in time detect that all components of the set take a state suited or required for conducting a calibration measurement. In response to the detection of such a state pattern, the calibration module may initiate the calibration measurement and take inside temperature values and/or determine compensated ambient temperature values. In another variant, the two above variants are mixed. For example, in response to detecting that components of a subset of the set already take a state suited or required for conducting the calibration measurement, the states of the remaining components are effected into the state required for conducting the calibration measurement. For example, for a smart phone the set may include the components central processing unit, energy storage, display and radio frequency transceiver. During operation, it may be detected that the display and the radio frequency transceiver as well as the energy storage are inactive, which may be interpreted that the smart phone currently is neither used nor recharged. If an inactive state of these three components is required for a calibration measurement the chance may be taken and a defined load, such as a defined number of processes may be applied to the central processing unit initiated by the calibration engine.

While for some components it is sufficient to switch into the single active state available, it is preferred to apply a defined electrical load to the subject component/s. For example, in case the first component is the central processing unit, a defined load may be initiated which in one embodiment may be represented by the number of processes executed by the central processing unit.

In a preferred embodiment, the component is effected into an active state is the component of the set the one of the other temperature sensors is assigned to for sensing a temperature of this component. Hence, an immediate impact of the heat radiated by this component can be sensed without the need to respect heat propagation to more remote locations of temperature sensor/s. In another preferred embodiment, the calibration measurement is only executed when it is detected that the device is presently recharged. It is preferred that the device has a rechargeable energy storage for supplying energy for the device operations. Given that during the calibration measurement a high electrical load is applied to at least the first component of the set for radiating a high amount of heat, the calibration measurement may consume lots of energy. If such calibration measurement would be executed while the energy storage is not recharged, the energy storage may be discharged after the calibration measurement which state may not be appreciated by the user. It may be preferred that the execution of the calibration measurement including the activation of the subject components is only executed during the energy storage being recharged. For this purpose, it may be detected if the device is connected to a charging cable or if a charging current is present.

The calibration measurement may generally be executed soon after start running the device for the first time, and/or thereafter in regular intervals, and/or when suited states of at least some of the components are detected.

The set of calibration parameters may include at least one calibration parameter which, for example, may be applied to the sensed inside temperature. The set may preferably include a calibration parameter assigned to each other temperature sensor, or may even contain multiple calibration parameters for each other temperature sensor. In a preferred embodiment, the calibration parameter assigned to a dedicated other temperature sensor may adjust the, and in one embodiment be multiplied by the inside temperature sensed by this other temperature sensor such that finally the compensated ambient temperature is determined dependent on the adjusted sensed inside temperature/s, and dependent on the sensed ambient temperature which of course may also include a sensed ambient temperature adjusted by an associate calibration parameter.

In an embodiment, in response to the one or more active components radiating heat during a calibration measurement, and by means of a thermal model of the device that models the heat flux from the components to the location/s of the other temperature sensor/s, expected inside temperature/s at these s location/s may be determined upfront, or can be sensed upfront by means of ideal temperature sensors, and be made available to the calibration module. The inside temperature/s sensed during or in response to the calibration measurement can then be compared to the expected inside temperature/s for the subject location/s. A calibration parameter for an inside temperature sensed at a given location may be derived from a deviation between the sensed inside temperature during the calibration measurement and the expected inside temperature. This is preferably achieved for each other sensor. The expected inside temperature/s may be stored as a function of the ambient temperature for taking into account that the calibration measurement may be taken at different ambient temperatures. The ambient temperature may be sensed prior to the calibration measurement, i.e. without the impact of excessive heat radiated.

In another variant, it is preferred that during the calibration measurement the ambient temperature is measured by the corresponding temperature sensor. This measurement is affected by the heat radiated by at least the first component. A compensated ambient temperature is determined based on the sensed ambient temperature and based on the sensed inside temperatures which may suffer from offset etc. In addition, by means of the underlying thermal model, an expected compensated ambient temperature is determined upfront based on the heat transferred from at least the first component to the temperature sensor for sensing the ambient temperature. Hence, a deviation of the compensated ambient temperature determined for the given load pattern from the expected compensated ambient temperature allows for deriving the calibration parameters. For enhancing the determination of the set of calibration parameters, the expected compensated ambient temperature may be recorded dependent on the ambient temperature. Then the expected compensated ambient temperature may be selected subject to the ambient temperature sensed by the corresponding temperature sensor e.g. prior to applying the load pattern for calibration purposes to the subject components of the set.

Preferably, the portable electronic device may be one of a mobile phone, and especially a smart phone, a handheld computer, an electronic reader, a tablet computer, a game controller, a pointing device, a photo or a video camera, a computer peripheral.

According to another aspect of the present invention, a method is provided for operating a portable electronic device. The portable electronic device contains a set of components radiating heat in an active state in response to the consumption of electrical energy. An ambient temperature of the portable electronic device is sensed by means of a temperature sensor. At least one temperature inside the portable electronic device is sensed by at least one other temperature sensor. A calibration measurement is conducted for determining a set of calibration parameters for adjusting the at least one sensed inside temperature. The calibration measurement is conducted during or in response to an active state of at least a first component of the set. A compensated ambient temperature is determined dependent on at least the sensed ambient temperature and dependent on the at least one adjusted sensed inside temperature.

In a preferred example, the adjusted sensed inside temperature may be dependent on the sensed inside temperature $T_1$ and the calibration parameter $c1$ as follows:

$$\text{adjusted sensed inside temperature} = T_1 + c1 * T_1$$

According to a further aspect of the present invention, a computer program element is provided for operating a portable electronic device, which computer program element, which preferably is stored on a computer storage medium, comprises computer program code means for executing a method according to any of the embodiments of the present invention.

Other advantageous embodiments are listed in the dependent claims as well as in the description below. The described embodiments similarly pertain to the device, the method, and the computer program element. Synergetic effects may arise from different combinations of the embodiments although they might not be described in detail.

Further on it shall be noted that all embodiments of the present invention concerning a method might be carried out in the order of the steps as described. Nevertheless this has not to be the only essential order of steps but all different orders of the method steps shall be comprised in the scope of the claims and be disclosed by the method claims.

For example, the temperature values for the calibration may be taken in response to activating at least the first component, respectively soon after when having reached a steady state. However, in case the first component is not the central processing unit, an evaluation of the sensed temperature values which typically is conducted by the central processing unit, may be taken offline from the calibration heating in case it is not desired to switch on the central processing unit in combination with or soon after to the first component. Instead, the sensed inside and ambient temperature values may be stored in response to their taking such that the next time the central processing unit will be activated by a user or a process, the set of calibration parameters may then be determined by means of the central processing unit based on the stored inside and ambient temperature values. For the time in between, the compensator may continue to work with previously determined calibration parameters, for example.

BRIEF DESCRIPTION OF THE DRAWINGS

The detailed description refers to embodiments of the present invention. Such description makes reference to the annexed drawings, wherein.

DETAILED DESCRIPTION

Figure 1:
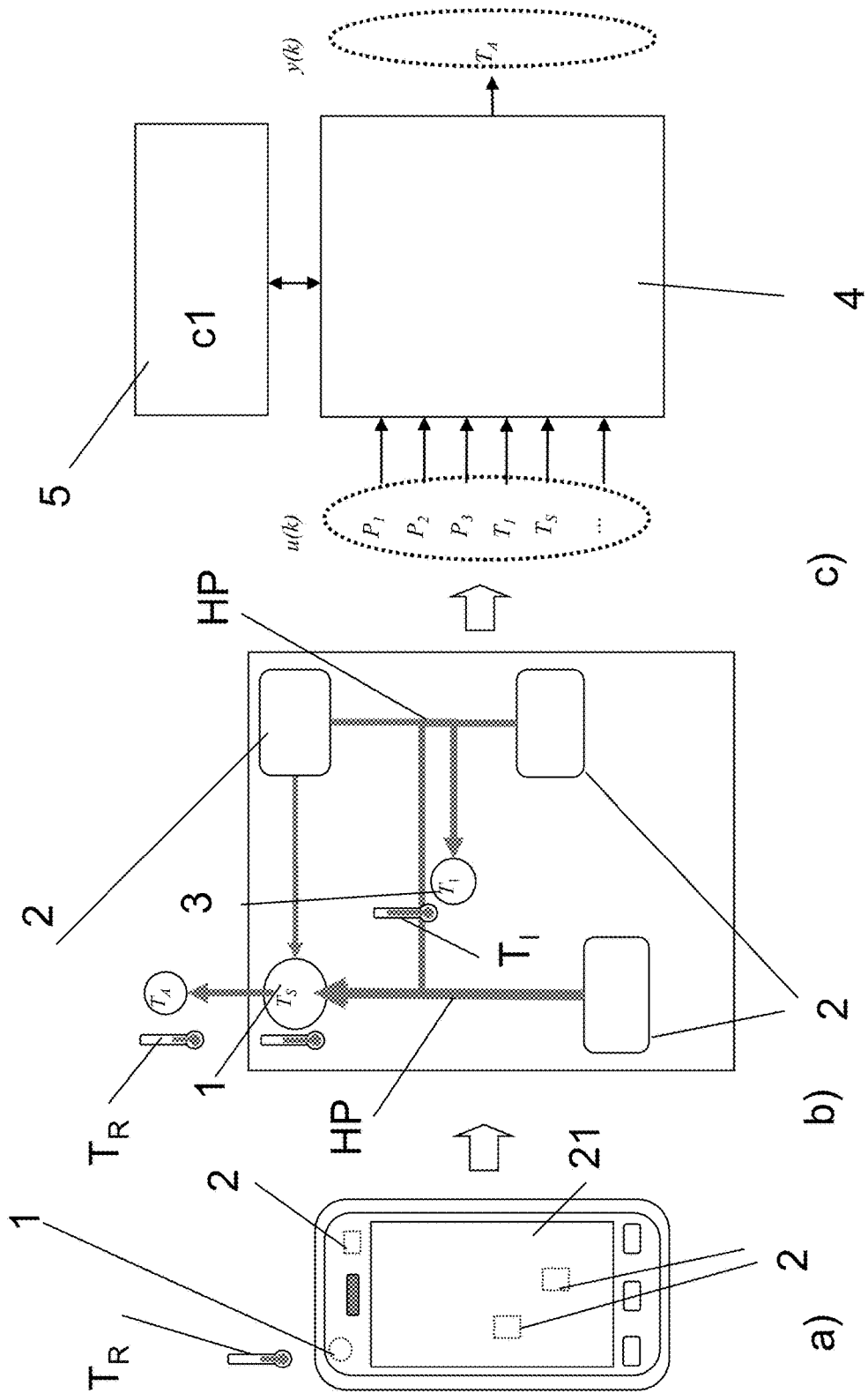
FIG. 1 illustrates a mobile phone according to an embodiment of the present invention in diagram a), an associated thermal block diagram in diagram b), and an associate compensator in diagram c)

FIG. 1a) shows a diagram illustrating a mobile phone according to an embodiment of the present invention. The mobile phone includes a temperature sensor 1 and several components 2 generating heat during operation of the mobile phone, such as a display 21. The temperature sensor 1 provides a sensed ambient temperature $T_S$.

The temperature sensor 1 itself may not provide the real ambient temperature $T_R$ but a sensed ambient temperature $T_S$ deviating from the real ambient temperature $T_R$ because of a self-heating of the device that perturbs the internal temperature sensor 1. Hence, the signal of the integrated temperature sensor 1 is compensated for this effect. The compensator preferably uses information of one or more other temperature sensors 3 for sensing a temperature $T_1$ inside the device, one of which other temperature sensors 3 is depicted in FIG. 1a). Such other temperature sensor 3 senses a temperature at the subject location and as this qualifies for determining an impact of heat, e.g. generated by components arranged close to the other temperature sensor 3 onto the ambient temperature sensed by the temperature sensor 1. However, the other temperature sensor 3 may not provide the real inside temperature $T_1$ either but a sensed inside temperature $T_1$ deviating from the real inside temperature $T_1$ owed to offset or other drift effects, for example. In addition to the one or more sensed inside temperatures $T_1$, information related to the power consumed by one or more of the components 2 may serve as input to the compensation model. Moreover, the heat propagation in time towards the temperature sensor 1 may also be reflected in the thermal compensation model such that its influence can be compensated from the sensed ambient temperature. Summarizing, the real ambient temperature $T_R$ is desired to be estimated by the portable electronic device by determining a compensated ambient temperature $T_A$.

In diagram 1b), a "thermal" block diagram of the mobile phone of diagram 1a) is shown in which the heat generating components 2 are connected to the temperature sensor 1 and to each other by heat paths HP on which heat flux is propagated. Preferably, such heat flux propagating to the temperature sensor 1 may be determined and be compensated for at the temperature sensor 1 by a compensator 4 as is shown in diagram 1c). The compensator 4 may be an entity, represented by hardware, software, or a combination of both, which receives the sensed ambient temperature $T_S$, the sensed inside temperature $T_1$, and information $P_1$, $P_2$, $P_3$ related to the power consumption of the three components 2 identified as most crucial in impacting the sensed ambient temperature $T_S$. The compensator 4 supplies at its output the compensated ambient temperature $T_A$. A calibration module is schematically referred to as 5.

In general, the compensator 4 may make use of a dynamic thermal model of the mobile device such as, for example, is shown in diagram 1b). The dynamic thermal model may mathematically be described by a differential equation system. The model may in one embodiment comprise one or more, and preferably the most relevant heat sources, and in another embodiment additionally one or more, and preferably the most relevant thermal conductivities, and in another embodiment additionally one or more, and preferably the most relevant heat capacities, as well as it comprises the temperature sensor that is well coupled to the ambient, and it may comprise one or more optional temperature sensors that may be available in the mobile device.

The compensated ambient temperature $T_A$ may then be estimated from these inputs by using the following Equation 1) as compensator 4:

$$x(k+1)=Ax(k)+Bu(k)$$

$$y(k)=Cx(k)+Bu(k) \qquad \text{Collectively Equation 1)}$$

with u(k) denoting the inputs at time step k, y(k) denoting the output $T_A$, and x(k) denoting an internal state vector. A is an n-by-n matrix, B an n-by-m matrix, C an 1-by-n matrix and D an 1-by-m matrix, where n is the number of states that depends on the complexity of the model and m the number of inputs. Typical inputs may be, for example, an intensity of a display, a time derivative of a battery charge level, a central processing unit load, or other power management information. Additional temperature sensors at hot spots of the portable electronic device may improve the compensation results.

Hence, in one embodiment, the portable electronic device is modelled as a thermal system with heat sources, and optionally with heat capacities and/or thermal conductivities. From this model, a time-discrete compensator according to the state space description of Equation 1) is derived, that can easily be implemented on a microprocessor of the portable electronic device by using the following software code:

```
while not stopped
{
    u=Read_Input( );      // Read input
    y=C*x+D*u;            // Calculate output
    x=A*x+B*u;            // State Update
    T_A=y;                // Ambient Temperature = y
}
```

The compensated ambient temperature $T_A$ may be displayed on the display 21.

Figure 2:
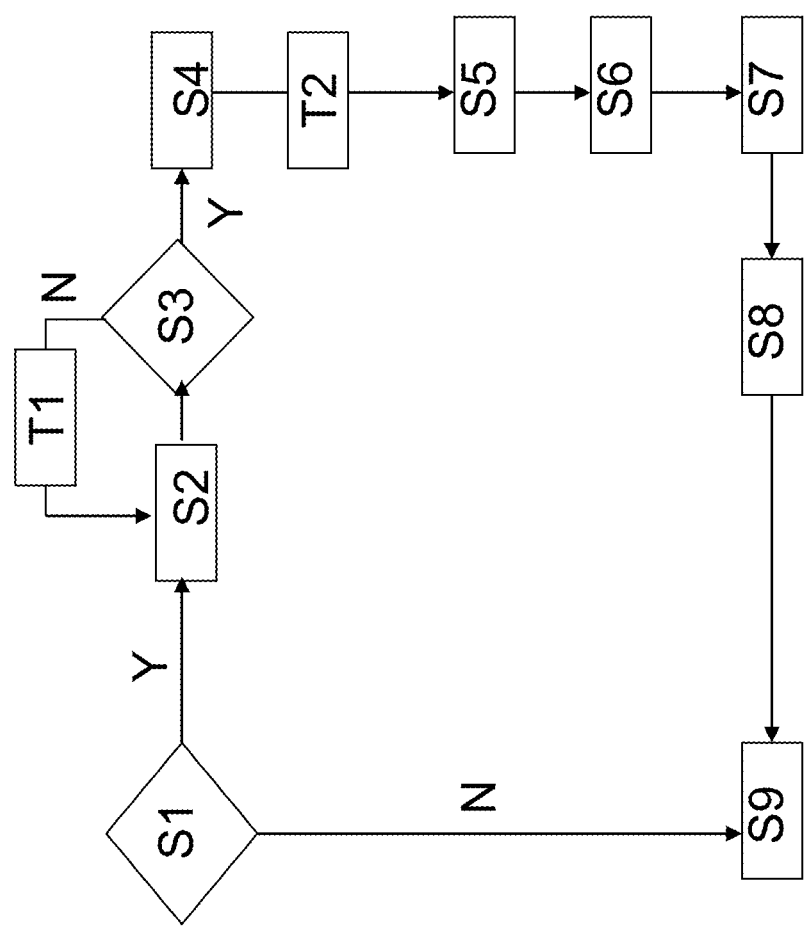
FIG. 2 shows a flowchart of a method according to an embodiment of the present invention.

FIG. 2 illustrates a flow chart of a method according to an embodiment of the present invention. In step S1 a flag is verified which flag indicates if calibration parameters for temperatures sensed inside a casing of a portable electronic device shall be determined. If so (Y), in step S2 the present state of a set of electrical energy consuming components of the portable electronic device is detected. The present set shall, for example, include a central processing unit, a display, an energy storage and a radio frequency (RF) transceiver. In step S3, it is verified if the state of the display, the energy storage and the RF transceiver each is inactive. If this is not the case (N), it is waited for a given time T, e.g. for five hours, until the then present states of all the components of the set are determined again. If the state of the subject three components is verified to be inactive (Y) in step S3, a defined load is applied to the central processing unit in step S4. While the load is continued to be upheld it is waited for time T2, e.g. for one minute, until the ambient temperature is sensed by means of an assigned temperature sensor and the inside temperature values are taken in step S5. In step S6, a compensated ambient temperature is calculated based on the sensed ambient temperature and the inside temperatures sensed in response to applying the load to the central processing unit, and in step S7 the compensated ambient temperature is compared to an expected compensated ambient temperature. The set of calibration parameters is derived from a deviation of the compensated ambient temperature from the expected compensated ambient temperature. In step S8, the load applied to the central processing unit is switched off again. In the following, it can be switched to a regular temperature sensing mode in step S9, wherein the temperature sensor and the other temperature sensors provide temperature values to a compensation model which determines a compensated ambient temperature based on these inputs and based on the calibration parameters applied to the sensed inside temperatures.

While there are shown and described presently preferred embodiments of the invention, it is to be distinctly understood that the invention is not limited thereto but may be otherwise variously embodied and practiced within the scope of the following claims.

The invention claimed is:

1. Portable electronic device, comprising
a temperature sensor for sensing an ambient temperature of the portable electronic device,
at least one other temperature sensor for sensing a temperature inside the portable electronic device,
a set of components radiating heat in an active state in response to the consumption of electrical energy,
a calibration module adapted to conduct a calibration measurement during or in response to an active state of at least a first component of the set, and adapted to determine a set of calibration parameters in response to the calibration measurement for adjusting the at least one sensed inside temperature, and
a compensator for determining a compensated ambient temperature dependent on at least the sensed ambient temperature and the at least one adjusted sensed inside temperature,
a) wherein at least one calibration parameter of the set is determined dependent on a compensated ambient temperature determined dependent on the ambient temperature sensed during the calibration measurement and dependent on the at least one inside temperature sensed during the calibration measurement and wherein the at least one calibration parameter of the set is determined dependent on a deviation of the determined compensated ambient temperature from an expected compensated ambient temperature, or
b) wherein at least one calibration parameter of the set is determined dependent on an inside temperature ($T_1$) sensed during the calibration measurement and wherein the at least one calibration parameter is determined dependent on a deviation of the inside temperature sensed during the calibration measurement from an upfront determined expected inside temperature.

2. Portable electronic device according to claim 1,
wherein the calibration module is adapted to apply a defined electrical load to at least the first component of the set for conducting the calibration measurement.

3. Portable electronic device according to claim 1,
comprising a rechargeable energy storage for supplying energy to the portable electronic device,
wherein the calibration module is adapted to detect a recharging process of the energy storage as a precondition for conducting the calibration measurement.

4. Portable electronic device according to claim 1,
wherein the set of components includes one or more, or all of a central processing unit, an energy storage, a display, a radio frequency transmission unit, and a global positioning unit.

5. Portable electronic device according to claim 1,
wherein the set of components includes at least a central processing unit, and
wherein the calibration module is adapted to apply a defined electrical load to the central processing unit for conducting the calibration measurement.

6. Portable electronic device according to claim 1,
wherein the at least one other temperature sensor is arranged for sensing a temperature of an assigned component of the set, and
wherein the calibration module is adapted to apply a defined electrical load to the first component for conducting the calibration measurement.

7. Method for operating a portable electronic device containing a set of components radiating heat in an active state in response to the consumption of electrical energy, comprising
sensing an ambient temperature of the portable electronic device by means of a temperature sensor,
sensing at least one temperature inside the portable electronic device by at least one other temperature sensor,
conducting a calibration measurement for determining a set of calibration parameters for adjusting the at least one sensed inside temperature,
conducting the calibration measurement during or in response to an active state of at least a first component of the set, and
determining a compensated ambient temperature dependent on at least the sensed ambient temperature and dependent on the at least one adjusted sensed inside temperature,
a) wherein at least one calibration parameter of the set is determined dependent on a compensated ambient temperature determined dependent on the ambient temperature sensed during the calibration measurement and dependent on the at least one inside temperature sensed during the calibration measurement and wherein the at least one calibration parameter of the set is determined dependent on a deviation of the determined compensated ambient temperature from an expected compensated ambient temperature, or
b) wherein at least one calibration parameter of the set is determined dependent on an inside temperature ($T_1$) sensed during the calibration measurement and wherein the at least one calibration parameter is determined dependent on a deviation of the inside temperature sensed during the calibration measurement from an upfront determined expected inside temperature.

8. Method according to claim 7,
wherein the calibration measurement is conducted only during a recharging process of a rechargeable energy storage of the portable electronic device.

9. Method according to claim 7,
wherein a defined electrical load is applied to at least the first component of the set for conducting the calibration measurement.

10. Method according to claim 7,
wherein the set includes at least two components, and
wherein a defined electrical load is applied to a first component of the set and no load is applied to the other components of the set for conducting the calibration measurement.

11. Method according to claim 10,
wherein the set includes at least a central processing unit, a display and a radio frequency transceiver, and wherein a defined electrical load is applied to the central processing unit and no load is applied to the display and the radio frequency transceiver for conducting the calibration measurement.

12. Method according to claim 7,
wherein the set of components includes at least a rechargeable energy storage of the portable electronic device, and
wherein a defined electrical load is applied to the energy storage for conducting the calibration measurement.

13. Method according to claim 7, comprising
detecting states of the components of the set suited for conducting the calibration measurement, and
in response to the detection of the suited states conducting the calibration measurement.

14. Method according claim 7, comprising
detecting states of a subset of components of the set suited for conducting the calibration measurement, and
effecting components other than the components in the subset into states suited for conducting the calibration measurement.

15. A non-transitory, tangible computer readable storage medium for operating a portable electronic device, containing computer program code for implementing a method according to claim 7 when executed on a central processing unit of the portable electronic device.

* * * * *